United States Patent
Bergman et al.

(10) Patent No.: US 11,567,071 B2
(45) Date of Patent: Jan. 31, 2023

(54) DEVICES AND METHODS FOR LATERAL FLOW TESTS OF BODILY FLUIDS

(71) Applicant: FRESENIUS MEDICAL CARE HOLDINGS, INC., Waltham, MA (US)

(72) Inventors: Eric David Bergman, Newton, MA (US); Daniel Lewis Sloat, Wakefield, MA (US); Jonathan Fitzmaurice Leclerc, Northborough, MA (US); Rachel Lauren Bartels, Somerville, MA (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 0 days.

(21) Appl. No.: 17/495,034

(22) Filed: Oct. 6, 2021

(65) Prior Publication Data

US 2022/0120742 A1    Apr. 21, 2022

Related U.S. Application Data

(60) Provisional application No. 63/093,011, filed on Oct. 16, 2020.

(51) Int. Cl.
  *G01N 33/543*    (2006.01)
(52) U.S. Cl.
  CPC .............. *G01N 33/54388* (2021.08)
(58) Field of Classification Search
  None
  See application file for complete search history.

(56) References Cited

U.S. PATENT DOCUMENTS

| 9,074,920 | B2 | 7/2015 | Mendels et al. |
| 2003/0022392 | A1* | 1/2003 | Hudak .................... B01L 3/502 |
| | | | 436/518 |
| 2007/0224701 | A1 | 9/2007 | Rosenstein |
| 2010/0028204 | A1* | 2/2010 | Lee ........................ B01L 3/502 |
| | | | 422/68.1 |
| 2010/0226822 | A1 | 9/2010 | Ramel et al. |
| 2012/0244529 | A1 | 9/2012 | Fuchs et al. |
| 2012/0270225 | A1 | 10/2012 | Wakeley et al. |
| 2014/0370502 | A1 | 12/2014 | Brennan et al. |
| 2015/0010992 | A1 | 1/2015 | Fleming et al. |
| 2015/0011412 | A1 | 1/2015 | Deirmengian et al. |
| 2018/0094104 | A1 | 4/2018 | Carroll et al. |
| 2019/0079085 | A1 | 3/2019 | Lawrence et al. |

OTHER PUBLICATIONS

International Search Report and Written Opininon received for PCT Application Serial No. PCT/US2021/054623 dated Jan. 11, 2022, 7 pages.

* cited by examiner

*Primary Examiner* — Ann Montgomery
(74) *Attorney, Agent, or Firm* — Kilyk & Bowersox, P.L.L.C.

(57) ABSTRACT

The disclosed devices for lateral flow testing may include a receptacle for receiving bodily fluids from a patient that has a predetermined fluid volume for application to one or more lateral flow test strips. A test strip holder may be positioned to receive the predetermined fluid volume of the bodily fluids from the receptacle. Various other components, devices, and methods are also disclosed.

6 Claims, 8 Drawing Sheets

DEVICES AND METHODS FOR LATERAL FLOW TESTS OF BODILY FLUIDS

CROSS-REFERENCE TO RELATED APPLICATION

This application claims the benefit of U.S. Provisional Patent Application No. 63/093,011, titled "DEVICES AND METHODS FOR LATERAL FLOW TESTS OF BODILY FLUIDS," filed 16 Oct. 2020, the entire disclosure of which is incorporated herein by reference.

BACKGROUND

Peritonitis is a major cause of morbidity and mortality in peritoneal dialysis ("PD") patients globally. According to the International Society for Peritoneal Dialysis guidelines, peritonitis can be diagnosed when at least two of the following are present: (1) clinical features consistent with peritonitis, e.g., abdominal pain and/or cloudy dialysis effluent; (2) dialysis effluent with a white blood cell count greater than 100/μL or greater than $0.1 \times 10^9$/L (after a dwell time of at least two hours), with more than 50% of the white blood counts being polymorphonuclear; and (3) a positive peritoneal dialysis effluent culture.

In practice, when a patient presents in the clinic with symptoms of peritonitis, it typically takes clinicians from a couple of hours to five days to get the results of a white blood cell count and peritoneal dialysis effluent cell culture. There is also about a 10% culture-negative rate even with infections.

Once an infection diagnosis is made (without knowing the specific causative agent(s)), the nephrologist typically initiates empirical antibiotic therapy. Such therapy typically includes administering at least two different broad-spectrum antibiotics which collectively cover most of the gram-positive and gram-negative bacteria, along with an antifungal agent to prevent secondary fungal peritonitis until the causative agent(s) and drug susceptibility tests become available.

Lateral flow tests (also commonly referred to as "lateral flow assays") to diagnose peritonitis or other conditions have been developed. Generally speaking, a lateral flow test for peritonitis or other conditions are performed by placing a bodily fluid (also referred to as an "analyte") that may contain a target substance functioning as a marker for the condition on an end of a prepared test strip, laying the test strip on a horizontal surface, and allowing the analyte to wick across the test strip via capillary action. As the fluid proceeds, if the target substance is present in the analyte, the target substance reacts with bioactive particles (also referred to as "conjugates") and the combined target substance and bioactive particles proceed along the strip as the fluid proceeds. If a sufficient amount of the target substance is present, the combined target substance and bioactive particles congregate at a test line, and an indication (e.g., a color) of the presence of the target substance appears. If there is not enough (e.g., none) of the target substance in the analyte, then the indication does not appear at the test line or the indication is faint. Regardless of whether enough of the target substance is present in the analyte, a control indication may appear at a control line when the fluid reaches the control line, to indicate that the test was successfully completed.

If insufficient analyte is applied to the strip, the fluid may not reach the control line, and no control indication will appear at the control line. Without a control indication appearing, another test may be required. If too much analyte is applied, the test may show a false positive. Additionally or alternatively, too much analyte may result in an oversaturated test strip and/or spills, which can present a hazard particularly when the analyte is a bodily fluid.

BRIEF DESCRIPTION OF THE DRAWINGS

The accompanying drawings illustrate a number of example embodiments and are a part of the specification. Together with the following description, these drawings demonstrate and explain various principles of the present disclosure.

Throughout the drawings, identical reference characters and descriptions indicate similar, but not necessarily identical, elements. While the example embodiments described herein are susceptible to various modifications and alternative forms, specific embodiments have been shown by way of example in the drawings and will be described in detail herein. However, the example embodiments described herein are not intended to be limited to the particular forms disclosed. Rather, the present disclosure covers all modifications, equivalents, and alternatives falling within the scope of the appended claims.

DETAILED DESCRIPTION OF EXAMPLE EMBODIMENTS

The present disclosure is generally directed to devices and methods for lateral flow testing of bodily fluids, such as for peritonitis. In some examples, such devices may be configured to apply a predetermined, appropriate volume of a bodily fluid on a lateral flow test strip. For example, the device may include a first receptacle for receiving bodily fluids from a patient and a second receptacle configured to receive bodily fluids from the first receptacle. The first receptacle may include a first, relatively larger volume, and the second receptacle may include a second volume that is predetermined for application to one or more lateral flow test strips. In an additional example, the device may include a receptacle for receiving bodily fluids from a patient. The receptacle may have a predetermined fluid volume that is selected to be applied to at least one lateral flow test strip. An overflow chamber may be configured for receiving the bodily fluids in excess of the predetermined fluid volume (e.g., that may overflow from the receptacle).

These and other example embodiments may enable the application of an appropriate amount of bodily fluid analyte on the lateral flow test strip(s), without additional complexity for the user. For example, the devices of the present disclosure may receive an excess of bodily fluids without the user needing to precisely measure the amount applied or without needing to time the exposure of the test strip to the fluid. The device may automatically apply the appropriate amount of the analyte to the lateral flow test strip(s).

Features from any of the embodiments described herein may be used in combination with one another in accordance with the general principles described herein. These and other embodiments, features, and advantages will be more fully understood upon reading the following detailed description in conjunction with the accompanying drawings and claims.

The following will provide, with reference to FIGS. 1A-5, 7A, and 7B, detailed descriptions of devices for lateral flow testing of bodily fluids or other analytes, according to various embodiments of the present disclosure. With reference to FIGS. 6 and 8, the following will provide detailed descriptions of methods for lateral flow testing of bodily fluids, according to additional embodiments of the present disclosure.

Figure 1A:
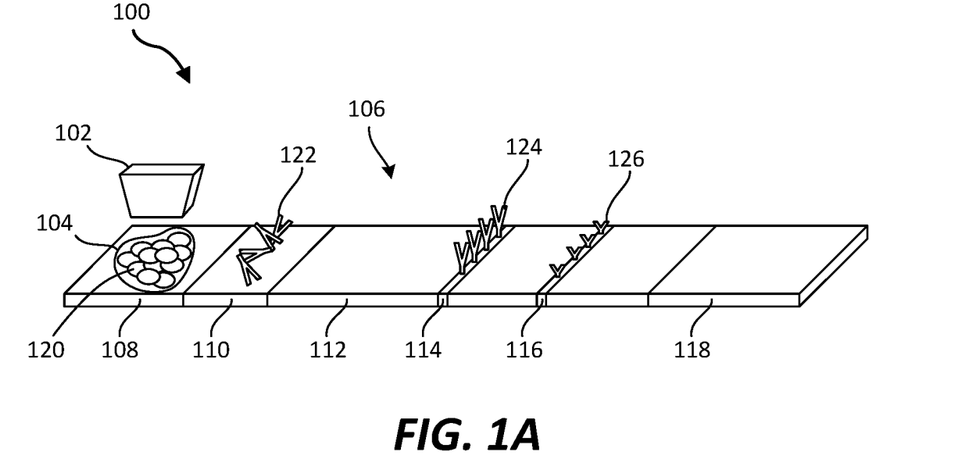
FIGS. 1A-1C are perspective diagrams of a device for lateral flow testing of bodily fluids at various stages of operation, according to at least one embodiment of the present disclosure.
Figure 1B:
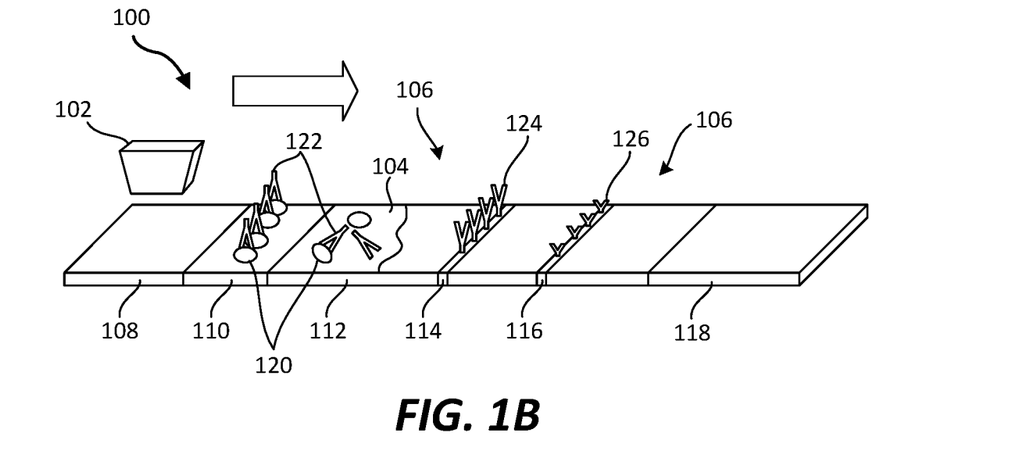
Figure 1C:
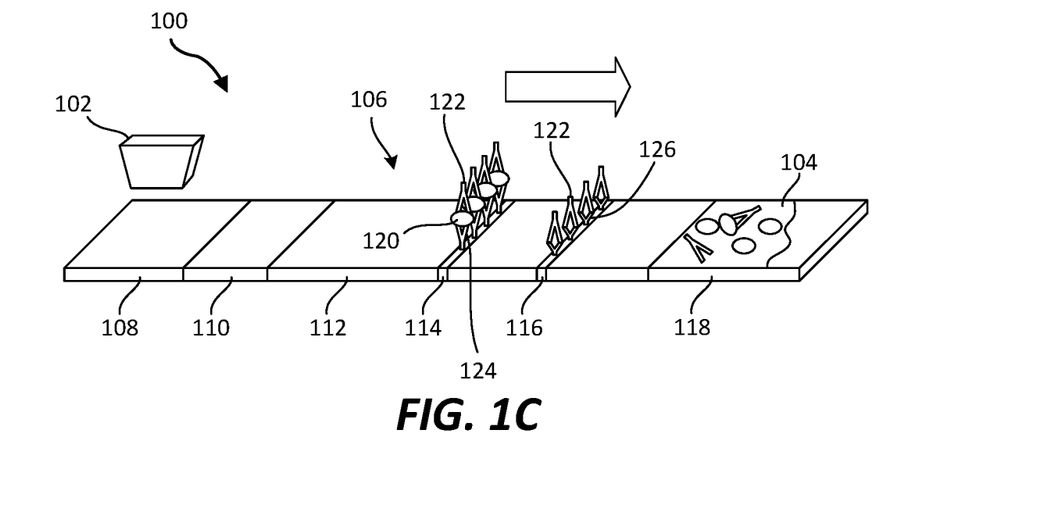

FIGS. 1A-1C are perspective diagrams of a device 100 for lateral flow testing of bodily fluids at various stages of operation, according to at least one embodiment of the present disclosure. Referring to FIG. 1A, the device 100 may include a receptacle 102 for an analyte 104 from a patient (e.g., a peritoneal dialysis patient) for testing for the presence of a marker for a condition (e.g., peritonitis). A lateral flow test strip 106 may be positioned for receiving the analyte 104 from the receptacle 102 in a well portion 108. The lateral flow test strip 106 may also include a conjugate pad 110, a membrane 112, a test line 114, a control line 116, and an absorbent pad 118.

The receptacle 102 may have a size and shape to hold a predetermined volume of the analyte 104 for application of an appropriate amount of the analyte 104 to the lateral flow test strip 106. Any analyte 104 in excess of the predetermined volume may be kept away (e.g., diverted away, held in another receptacle, etc.) from the lateral flow test strip 106. Some suitable examples for keeping excess analyte 104 away from the lateral flow test strip 106 are described below with reference to FIGS. 2-5, 7A, and 7B.

The analyte 104 may be a bodily fluid or any other fluid to be tested for the detection and/or quantification of a target substance 120 that may be in the analyte 104. For example, the analyte 104 may be or include a sample of blood, urine, saliva, effluent from a peritoneal dialysis treatment, etc., from a patient. The target substance 120 may be a marker for a condition, such as peritonitis, a pathogen, pregnancy, etc. For example, the target substance 120 may be or include an antibody, a protein, a hormone, an antigen, bacteria, a fungus, etc.

The well portion 108 may be an adsorbent pad configured to receive the analyte 104 and to prepare the analyte 104 (e.g., via a surfactant, buffer salt, etc.) for analysis by the lateral flow test strip 106.

The conjugate pad 110 may contain conjugates 122 (e.g., bioactive particles, such as antibodies) that may be reactive specifically to the target substance 120. For example, as shown in FIG. 1B, when the analyte 104 is conveyed along the lateral flow test strip 106, particles of the target substance 120 may be chemically bound to the conjugates 122. The conjugates 122 may include detectable particles, such as gold or latex microspheres for visual detection. Other detectable particles may also be used, such as fluorescent particles and/or magnetic particles. The conjugates 122 may be maintained in a functionally stable state prior to use, such as by coating the conjugates 122 in a water-soluble material, such as sucrose. When the analyte 104 reaches the conjugates 122, the sucrose or other coating may dissolve into water of the analyte 104, exposing and chemically activating the conjugates 122 for reaction (e.g., for chemically binding) with the target substance 120.

As illustrated in FIG. 1B, the membrane 112 may be configured to further convey the analyte 104 along the lateral flow test strip 106, such as by capillary action. The membrane may include, for example, a cellulose material or other porous material configured to convey the analyte 104 along the lateral flow test strip 106.

The test line 114 may be a region of the membrane 112 with immobilized anti-analyte particles 124, which may be selected to react with particles of the target substance 120 that have been bound to the conjugates 122. As illustrated in FIG. 1C, the bound target substance 120 and conjugates 122 may react with the anti-analyte particles 124 and may congregate along the test line 114. When the target substance 120 is present in the analyte 104 in sufficient quantities, a detectable signal may be produced along the test line 114. For example, a visible color (e.g., from colored particles of the conjugates 122), fluorescent line, magnetic line, etc., may appear along the test line 114 to indicate that a sufficient quantity of the target substance 120 is present in the analyte 104. If there is insufficient (e.g., no) target substance 120 in the analyte 104, then the conjugates 122 may be conveyed past the test line 114, since the anti-analyte particles 124 may be non-reactive with the conjugates 122 lacking the target substance 120.

The control line 116 may be a region of the membrane 112 with immobilized anti-conjugate particles 126, which may be selected to react with the conjugates 122. As illustrated in FIG. 1C, the conjugates 122 may react with the anti-conjugate particles 126 and may congregate along the control line 116. This may provide an indication that the lateral flow test strip 106 has successfully conveyed the analyte 104 across the test line 114, regardless of whether there is enough of the target substance 120 in the analyte 104 to form a positive indication on the test line 114. Thus, after the control line 116 indicates that the test has been completed, the test line 114 may be analyzed for a positive or negative result.

Any additional analyte 104 may be conveyed past the control line 116 to the absorbent pad 118. For example, the absorbent pad 118 may be a sponge or other porous material configured to soak up and contain additional analyte 104.

By way of example and not limitation, various lateral flow testing concepts will next be described. These lateral flow testing concepts may be combined with the device 100 and related concepts as described above. Other concepts known to those skilled in the art of lateral flow testing may also be used.

The antigen indicative of an inflammatory response in the peritoneum may be neutrophil gelatinase-associated lipocalin, interleukin 1, interleukin 6, interleukin 8, tumor necrosis factor α, procalcitonin, and/or C-reactive protein. Lipoteichoic acid is an antigen indicative of the presence of gram-positive bacteria. Lipopolysaccharide is an antigen indicative of the presence of gram-negative bacteria. β-glucan is an antigen indicative of the presence of a fungus. For diagnosing peritonitis, the pathogen may be at least one bacterium and/or fungus.

In some embodiments, the conjugates 122 may include a binding molecule that specifically binds an antigen indicative of the presence of a specific pathogen species. For use with a peritoneal dialysis effluent, the specific pathogen may be *Staphylococcus aureus, Pseudomonas* sp., *Staphylococcus epidermidis, Staphylococcus haemolyticus, Candida* sp., *Escherichia coli*, vancomycin-resistant enterococci, or combinations thereof.

In some examples, the lateral flow test strip 106 may include a buffer that specifically elutes antigen(s), such as in the well portion 108 of the lateral flow test strip 106. The buffer composition may be chosen to selectively stabilize the antigen and/or antigen-antibody complex, maintain pH, and/or maintain or disrupt structure or binding of the antigen-antibody complex.

In certain embodiments, the device 100 may be used to diagnose peritonitis in a patient by detecting, in a peritoneal dialysis effluent analyte, an antigen indicative of an inflammatory response having been launched in the peritoneum, detecting an antigen indicative of the presence of a gram-positive bacteria, detecting an antigen indicative of the presence of a gram-negative bacteria, and/or detecting an antigen indicative of the presence of a fungus.

In some embodiment, the analyte 104 may include a peritoneal dialysis effluent that is taken directly from the patient and applied to the device 100, or the peritoneal dialysis effluent may be concentrated, filtered, and/or enriched prior to application to the device 100. In certain embodiments, enrichment may be by, for example, placing the peritoneal dialysis effluent sample into a conical tube, followed by centrifugation of the sample, and treatment with, e.g., a lysis buffer, extraction buffer, and/or neutralization buffer. Enrichment of a peritoneal dialysis effluent sample for antigens may also be by use of an ultrafiltration ("UF") membrane (e.g., molecular weight cutoff 29,000). In another embodiment, a syringe may be used to pass/push the peritoneal dialysis effluent sample through a UF membrane instead of using a centrifuge.

Such diagnostic methods can be used to treat peritonitis in the patient by first diagnosing the patient as having peritonitis and then administering an appropriate antibiotic to the subject to treat the peritonitis in view of the diagnosis.

The concepts discussed above with reference to FIGS. 1A-1C may be employed in conjunction with any of the examples discussed below with reference to FIGS. 2-8.

Figure 2:
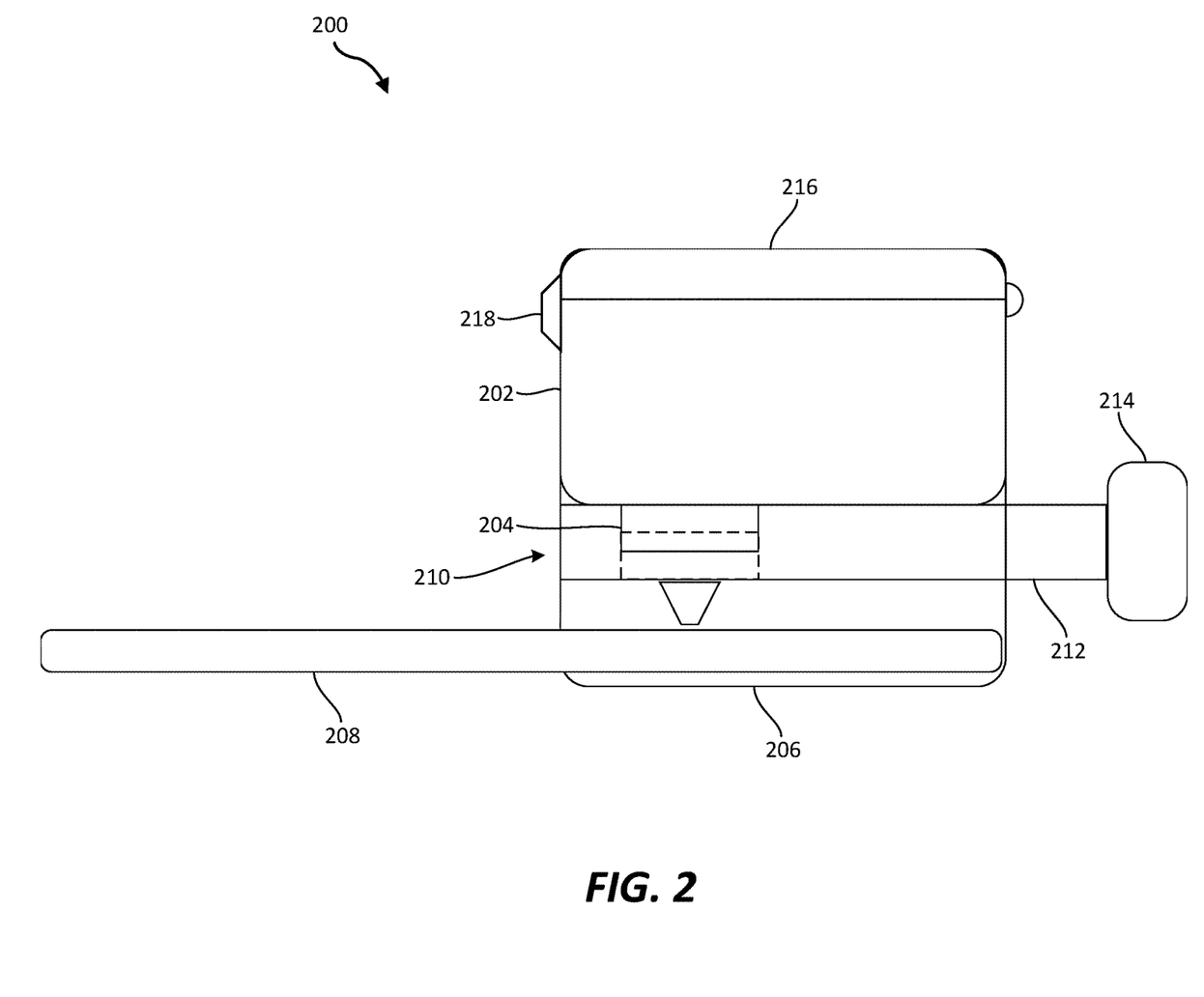
FIG. 2 is a cross-sectional side view of a device for lateral flow testing of bodily fluids, according to at least one embodiment of the present disclosure.

FIG. 2 is a cross-sectional side view of a device 200 for lateral flow testing of bodily fluids, according to at least one embodiment of the present disclosure. The device 200 may include a first receptacle 202 for receiving bodily fluids from a patient and a second receptacle 204 positioned for receiving a portion of the bodily fluids from the first receptacle 202. A test strip holder 206 may be positioned under the second receptacle 204 to receive the bodily fluids from the second receptacle 204.

The first receptacle 202 may have a first fluid volume, which may be larger than is needed to perform a successful lateral flow test. The second receptacle 204 may have a predetermined second fluid volume that is selected to be applied to at least one lateral flow test strip 208 inserted in the test strip holder 206. For example, the second fluid volume may be selected to apply a sufficient amount of the bodily fluids to the at least one lateral flow test strip 208 for a complete and successful test, but not so much that the lateral flow test strip(s) 208 become oversaturated.

In some examples, relational terms, such as "first," "second," "upper," "below," etc., may be used for clarity and convenience in understanding the disclosure and accompanying drawings and may not necessarily connote or depend on any specific preference, orientation, or order, except where the context clearly indicates otherwise.

Referring again to FIG. 2, the device 200 may also include a transfer mechanism 210 to move the bodily fluid from the second receptacle 204 to the test strip holder 206 and ultimately to the at least one lateral flow test strip 208. In the example shown in FIG. 2, the transfer mechanism 210 may include a rotating piston 212 that may be configured to rotate the second receptacle 204 from a first position (shown in FIG. 2 in solid lines) for receiving the bodily fluid from the first receptacle 202 to a second position (shown in FIG. 2 in dashed lines) for transferring (e.g., via gravity) the bodily fluid from the second receptacle 204 to the test strip holder 206. The rotating piston 212 may be biased (e.g., spring-biased) to the first position, such as to avoid inadvertent spilling of bodily fluids through the second receptacle 204 and test strip holder 206. In some embodiments, the rotating piston 212 may include a knob 214 to enable a user to grasp and rotate the rotating piston 212 into the second position after the bodily fluids are positioned in the first receptacle 202 and allowed to flow into the second receptacle 204.

In some embodiments, the first receptacle 204 may include a lid 216 for covering the first receptacle 204. The lid 216 may be configured to provide a fluid-tight seal (e.g., via an O-ring and a clasp 218), which may reduce or eliminate a chance of spilling the bodily fluids within the first receptacle 204 when the lid 216 is closed.

In some examples, the test strip holder 206 may be removable and replaceable relative to the first receptacle 202 and second receptacle 204. For example, the test strip holder 206 may be used with the first receptacle 202 and second receptacle 204 to test bodily fluids positioned within the first receptacle 202, and then the test strip holder 206 with its lateral flow test strip(s) 208 may be decoupled from the first receptacle 202 and second receptacle 204. A replacement test strip holder 206 with one or more unused lateral flow test strip(s) 208 may be coupled to the first receptacle 202 and second receptacle 204 to run another test on the bodily fluids within the first receptacle 202. Thus, multiple tests may be sequentially performed on the bodily fluids within the first receptacle 202, without the need for obtaining a new sample from the patient for each test.

In operation, a user may place bodily fluids to be tested within the first receptacle 202 and the lid 216 may be closed. The lateral flow test strip(s) 208 that are configured to detect one or more target substances may be positioned at least partially within the test strip holder 206. A portion of the bodily fluids may be allowed flow into the second receptacle 204. The user may rotate the knob 214 to transfer the predetermined second volume of the bodily fluids from the second receptacle 204 to the lateral flow test strip(s) 208. The bodily fluids may be conveyed along the lateral flow test strip(s) 208 and tested for the presence and/or quantity of the target substance(s), as described above with reference to FIGS. 1A-1C. After a given time (depending on the lateral flow test strip(s) 208 used), the lateral flow test strip(s) 208 may provide an indication of the presence and/or quantity of the target substance(s) in the bodily fluids. After the results of the test are obtained, the device 200, including any excess bodily fluids that may remain within the first receptacle 202, may be discarded, such as in an appropriate biohazard waste container.

Figure 3:
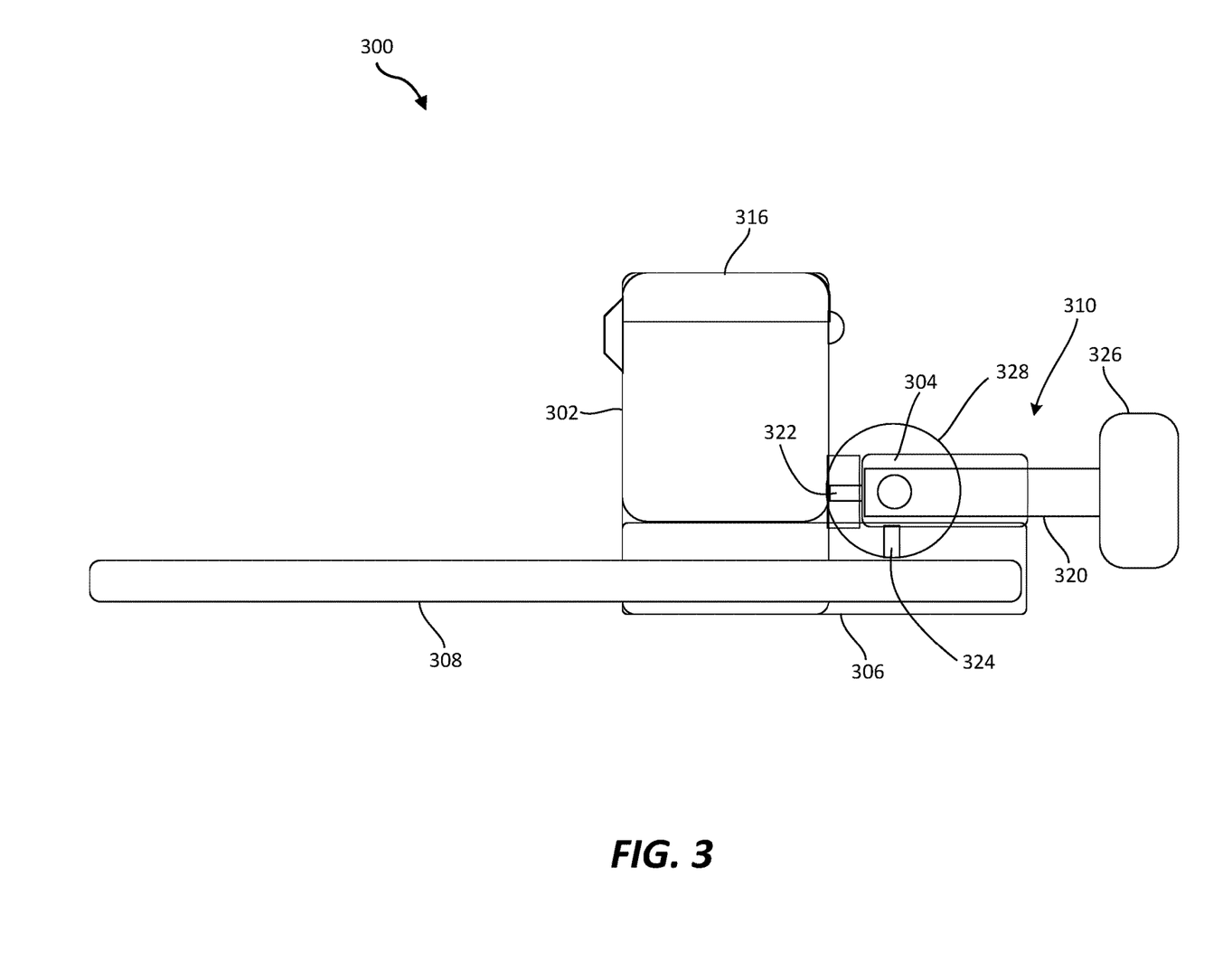
FIG. 3 is a cross-sectional side view of a device for lateral flow testing of bodily fluids, according to at least one other embodiment of the present disclosure.

FIG. 3 is a cross-sectional side view of a device 300 for lateral flow testing of bodily fluids, according to at least one other embodiment of the present disclosure. The device 300 may be similar to the device 200 described above with reference to FIG. 2. For example, the device 300 may include a first receptacle 302 having a first fluid volume, a second receptacle 304 having a predetermined second fluid volume for application to one or more lateral flow test strips 308, a test strip holder 306 for holding the lateral flow test strip(s) 308, and a transfer mechanism 310 for transferring the second fluid volume of the bodily fluids from the second receptacle 304 to the lateral flow test strip(s) 308 in the test strip holder 306. The first receptacle 302 may include a lid 316, such as to avoid spills of the bodily fluids from the first receptacle 302.

As shown in the example illustrated in FIG. 3, the transfer mechanism 310 may include a syringe 320 positioned and configured to withdraw the second fluid volume of the bodily fluids from the first receptacle 302. The second receptacle 304 may be defined by an internal volume of the syringe 320 when a plunger of the syringe 320 is fully withdrawn. A first one-way channel 322 (e.g., a first check valve) may be positioned between the first receptacle 302 and the second receptacle 304. The first one-way channel 322 may be configured to let fluid flow from the first receptacle 302 into the second receptacle 304, but may inhibit (e.g., prevent) the flow of fluid from the second receptacle 304 back into the first receptacle 304. A second one-way channel 324 (e.g., a second check valve) may be positioned between the second receptacle 304 and the test strip holder 306. The second one-way channel 324 may be configured to let fluid flow from the second receptacle 304 into the test strip holder 306, but may inhibit (e.g., prevent) the flow of fluid from the test strip holder 306 into the second receptacle 304. The syringe 320 may include a knob 326 for a user to grasp the syringe 320 to operate the device 300.

In additional embodiments, the syringe 320 may be mounted to a pivot 328. The second receptacle 304 may be in fluid communication with the first receptacle 302 when the syringe 320 and pivot 328 are in a first position (shown in FIG. 3). The syringe 320 may be rotated about the pivot 328 (e.g., in a counterclockwise direction from the perspective of FIG. 3) to orient the syringe 320 such that the second receptacle 304 is in fluid communication with the test strip holder 306.

In operation, a user may place bodily fluids to be tested within the first receptacle 302 and the lid 316 may be closed. The lateral flow test strip(s) 308 that are configured to detect one or more target substances may be positioned at least partially within the test strip holder 306. The user may grasp and pull the knob 326 to draw the second fluid volume of the bodily fluids with the syringe 320 from the first receptacle 302 through the first one-way channel 322 and into the second receptacle 304. In embodiments in which the syringe 320 is mounted to the pivot 328, the user may rotate the syringe 320 using the pivot from the first position to the second position. Whether or not the pivot 328 is present, the user may then push on the knob 326 to force the second fluid volume of the bodily fluids from the second receptacle 304 into the test strip holder 306 and ultimately onto the lateral flow test strip(s) 308. The bodily fluids may be tested for the presence and/or quantity of the target substance(s), as described above with reference to FIGS. 1A-1C. After a given time (depending on the lateral flow test strip(s) 308 used), the lateral flow test strip(s) 308 may provide an indication of the presence and/or quantity of the target substance(s) in the bodily fluids. After the results of the test are obtained, the device 300, including any excess bodily fluids that may remain within the first receptacle 302, may be discarded, such as in an appropriate biohazard waste container.

Figure 4:
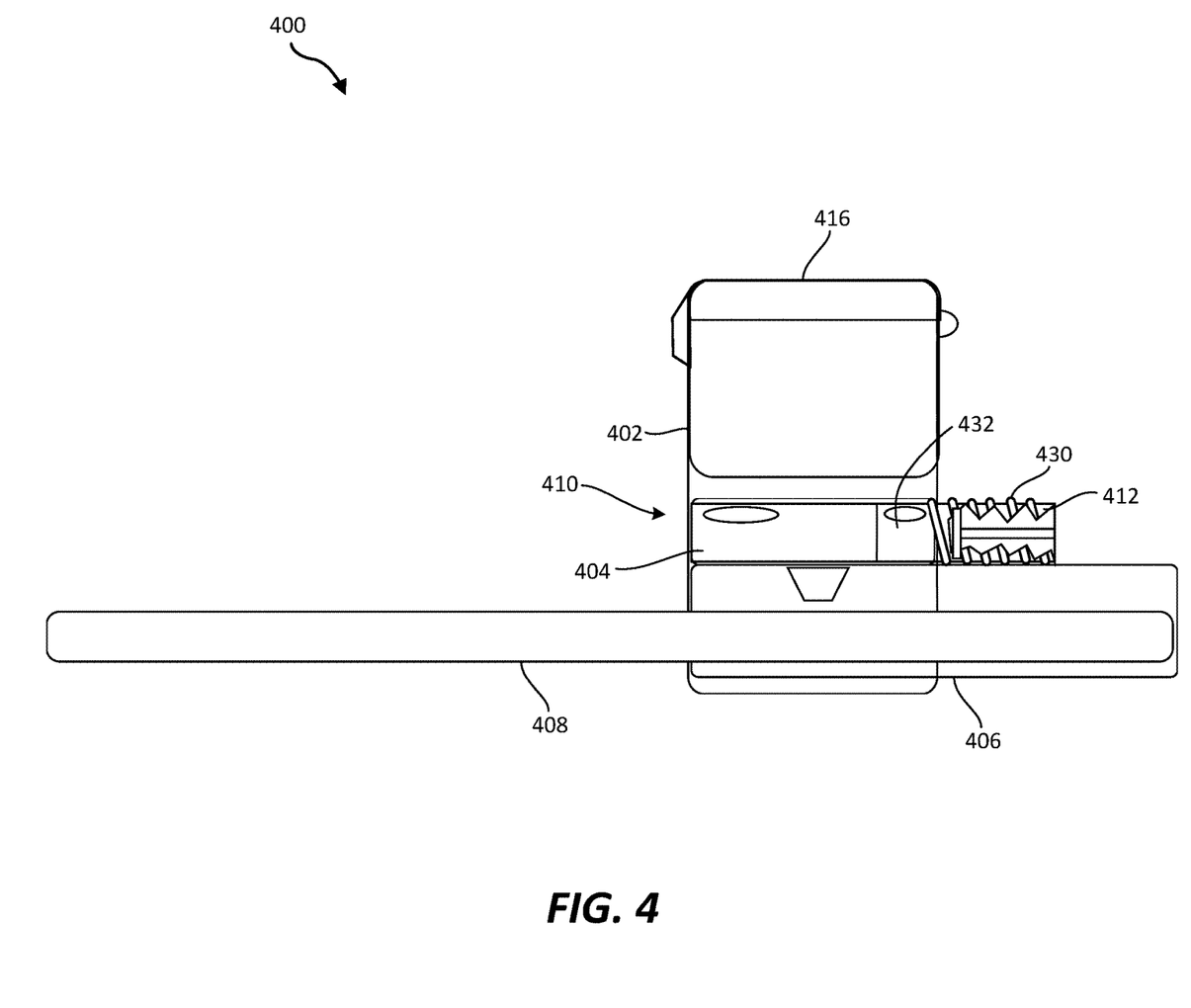
FIG. 4 is a cross-sectional side view of a device for lateral flow testing of bodily fluids, according to at least one additional embodiment of the present disclosure.

FIG. 4 is a cross-sectional side view of a device 400 for lateral flow testing of bodily fluids, according to at least one additional embodiment of the present disclosure. The device 400 may be similar to the device 200 described above with reference to FIG. 2. For example, the device 400 may include a first receptacle 402 having a first fluid volume, a second receptacle 404 having a predetermined second fluid volume for application to one or more lateral flow test strips 408, a test strip holder 406 for holding the lateral flow test strip(s) 408, and a transfer mechanism 410 for transferring the second fluid volume of the bodily fluids from the second receptacle 404 to the lateral flow test strip(s) 408 in the test strip holder 406. The first receptacle 402 may include a lid 416, such as to avoid spills of the bodily fluids from the first receptacle 402.

As shown in the example illustrated in FIG. 4, the transfer mechanism 410 may include a rotating piston 412 that may be rotated by interaction of the rotating piston 412 with a screw thread 430. In this embodiment, rotation of the rotating piston 412 may be initiated by a catalyst interacting with bodily fluids in a catalyst chamber 432. The interaction of the catalyst with the bodily fluids may cause the combined catalyst and bodily fluids to expand, forcing the piston to move linearly (e.g., to the right in the view of FIG. 4) and to interact with the screw thread 430, resulting in rotation of the rotating piston 412. In this example, the rotation of the rotating piston 412 may occur automatically, without manual manipulation by a user.

The catalyst in the catalyst chamber 432 may be any material or structure that expands upon interaction with the bodily fluids. For example, the catalyst may include a foam precursor that expands upon mixing with water in the bodily fluids. In additional examples, the catalyst may include a physical structure, such as a sponge, that expands upon exposure to and absorption of the bodily fluids.

In operation, the lateral flow test strip(s) 408 that are configured to detect one or more target substances may be positioned at least partially within the test strip holder 406. A user may place bodily fluids to be tested within the first receptacle 402 and the lid 416 may be closed. A portion (e.g., in the amount of the second fluid volume) of the bodily fluids from the first receptacle 402 may drop into the second receptacle 404 and another portion of the bodily fluids may drop into the catalyst chamber 432 via gravity. As the catalyst reacts with the bodily fluids in the catalyst chamber 432 and expands, the rotating piston 412 may be forced to move in a linear direction (e.g., to the right in the view of FIG. 4). As the rotating piston 412 is forced in the linear direction, the rotating piston 412 may press against a surface of the screw thread 430, causing the rotating piston 412 to rotate. The second fluid volume of the bodily fluids may then be transferred from the second receptacle 404 into the test strip holder 406 and ultimately onto the lateral flow test strip(s) 408. The bodily fluids may be tested for the presence and/or quantity of the target substance(s), as described above with reference to FIGS. 1A-1C. After a given time (depending on the lateral flow test strip(s) 408 used), the lateral flow test strip(s) 408 may provide an indication of the presence and/or quantity of the target substance(s) in the bodily fluids. After the results of the test are obtained, the device 400, including any excess bodily fluids that may remain within the first receptacle 402, may be discarded, such as in an appropriate biohazard waste container.

Figure 5:
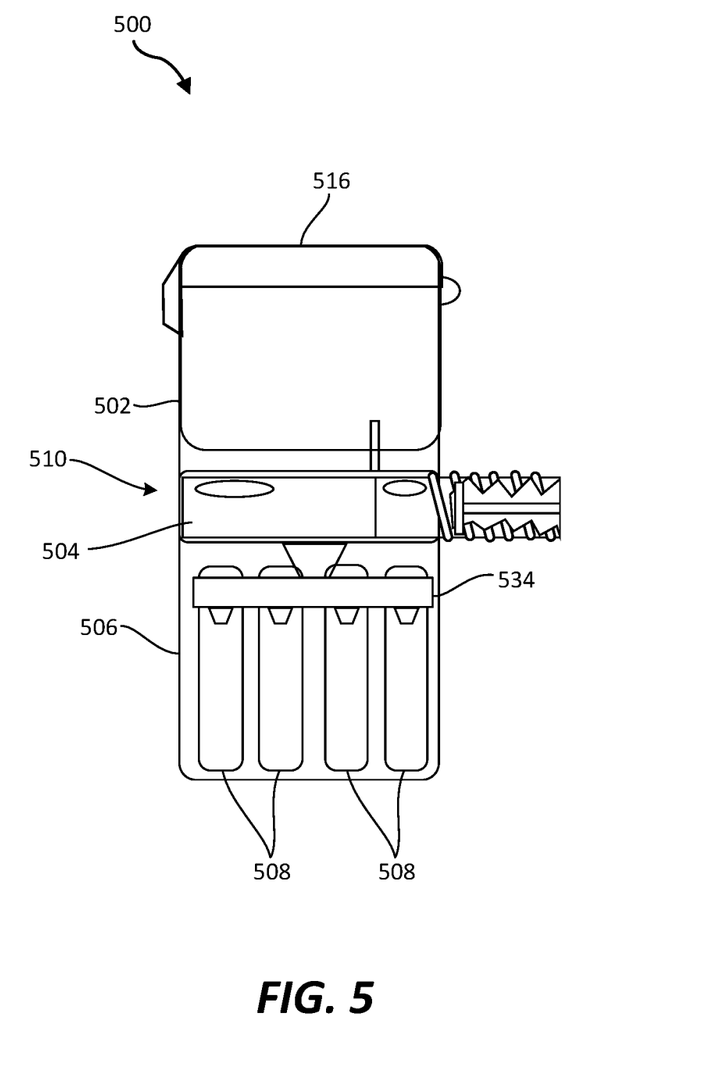
FIG. 5 is a cross-sectional side view of a device for lateral flow testing of bodily fluids, according to at least one other embodiment of the present disclosure.
Figure 6:
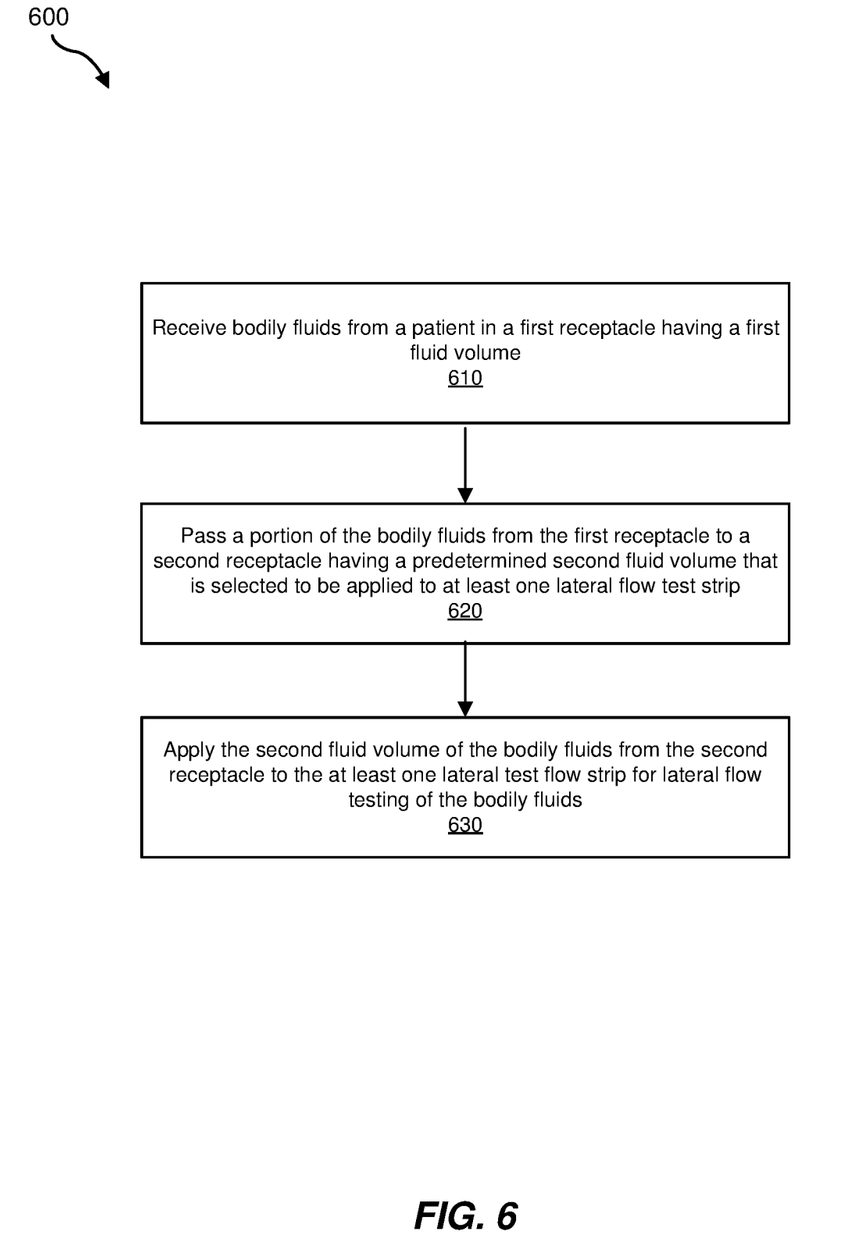
FIG. 6 is a flow chart illustrating a method of lateral flow testing of bodily fluids, according to at least one embodiment of the present disclosure.

FIG. 5 is a cross-sectional side view of a device 500 for lateral flow testing of bodily fluids, according to at least one other embodiment of the present disclosure. The device 500 may be similar to the device 200 described above with reference to FIG. 2. For example, the device 500 may include a first receptacle 502 having a first fluid volume, a second receptacle 504 having a predetermined second fluid volume for application to one or more lateral flow test strips 508, a test strip holder 506 for holding the lateral flow test strip(s) 508, and a transfer mechanism 510 for transferring the second fluid volume of the bodily fluids from the second receptacle 504 to the lateral flow test strip(s) 508 in the test strip holder 306. The first receptacle 502 may include a lid 516, such as to avoid spills of the bodily fluids from the first receptacle 502.

As shown in the example illustrated in FIG. 5, the device 500 may be configured for simultaneous application of an appropriate volume of the bodily fluids to multiple lateral flow test strips 508. By way of example and not limitation, the transfer mechanism 510 may include any of the transfer mechanisms 210, 310, 410 discussed above. When the transfer mechanism 510 is used to transfer the bodily fluids from the second receptacle 504 to the test strip holder 506, the bodily fluids may optionally be diverted and applied to the multiple lateral flow test strips 508 with a flow diverter 534. In some embodiments, the multiple lateral flow test strips 508 may be respectively configured for simultaneous testing for multiple different respective target substances in the bodily fluids. In this example, the second fluid volume in the second receptacle 504 may be selected based on the quantity of lateral flow test strips 508 to be positioned in the test strip holder 506.

FIG. 6 is a flow chart illustrating a method 600 of lateral flow testing of bodily fluids, according to at least one embodiment of the present disclosure. By way of example and not limitation, the method 600 may be performed using any of the devices 100, 200, 300, 400, 500 discussed above with reference to FIGS. 1A-5.

At operation 610, bodily fluids may be received from a patient in a first receptacle having a first fluid volume. Operation 610 may be performed in a variety of ways. For example, bodily fluids including at least one of blood, urine, saliva, and/or effluent from a peritoneal dialysis treatment may be received in the first receptacle. The bodily fluids may be introduced into the first receptacle by pouring, injection, flowing through a conduit, etc. By way of example, the bodily fluids may be received from the patient in a clinic (e.g., doctor's office, testing facility, etc.), in a care facility, or in the patient's home.

At operation 620, a portion of the bodily fluids may be passed from the first receptacle to a second receptacle. The second receptacle may have a predetermined second fluid volume that is selected to be applied to at least one lateral flow test strip. Operation 620 may be performed in a variety of ways. For example, the portion of the bodily fluids may be flowed into the second receptacle by gravity or by forcing the portion of the bodily fluids into the second receptacle (e.g., by drawing in the portion of the bodily fluids with a syringe).

At operation 630, the second fluid volume of the bodily fluids in the second receptacle may be applied to the at least one lateral flow test strip for lateral flow testing of the bodily fluids. Operation 630 may be performed in a variety of ways. For example, the bodily fluids may be flowed into a test strip holder via gravity or by forcing the bodily fluids from the second receptacle into the test strip holder (e.g., by compressing a syringe holding the bodily fluids). In some examples, a rotating piston including the second receptacle may be rotated from a first position for receiving the bodily fluids from the first receptacle to a second position for applying the bodily fluids from the second receptacle into the test strip holder and ultimately onto the lateral flow test strip(s). The bodily fluids from the second receptacle may be applied to a single lateral flow test strip or to multiple lateral flow test strips.

Figure 7A:
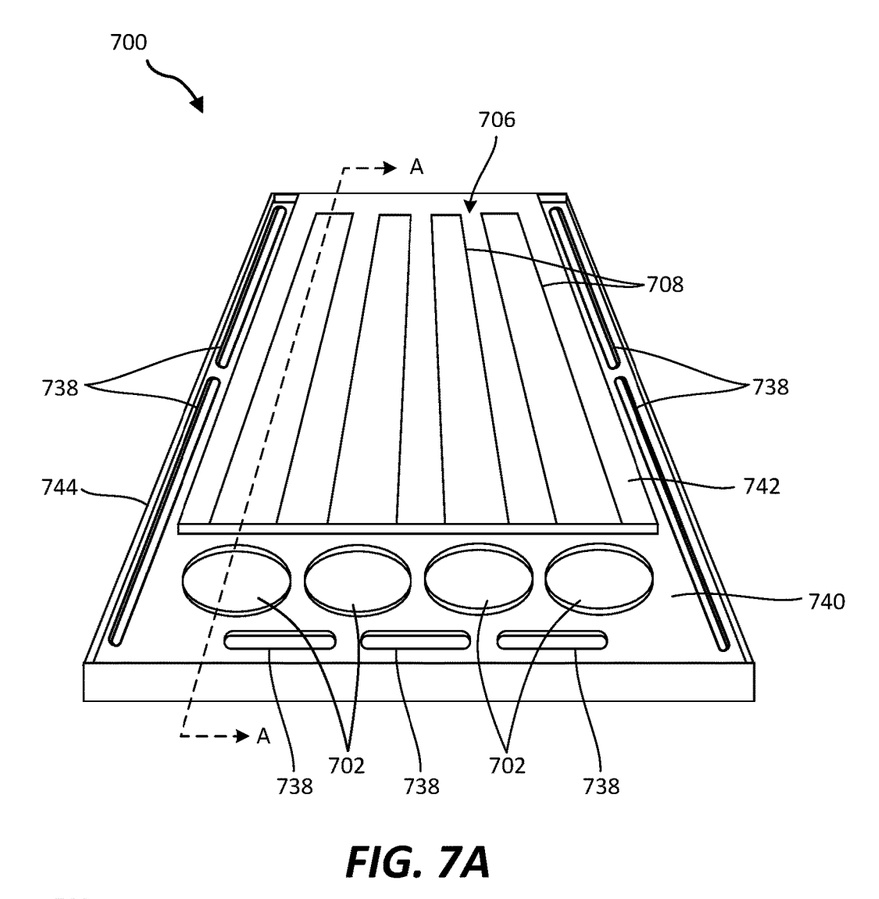
FIG. 7A is a perspective view of a device for lateral flow testing of bodily fluids, according to at least one additional embodiment of the present disclosure.
Figure 7B:
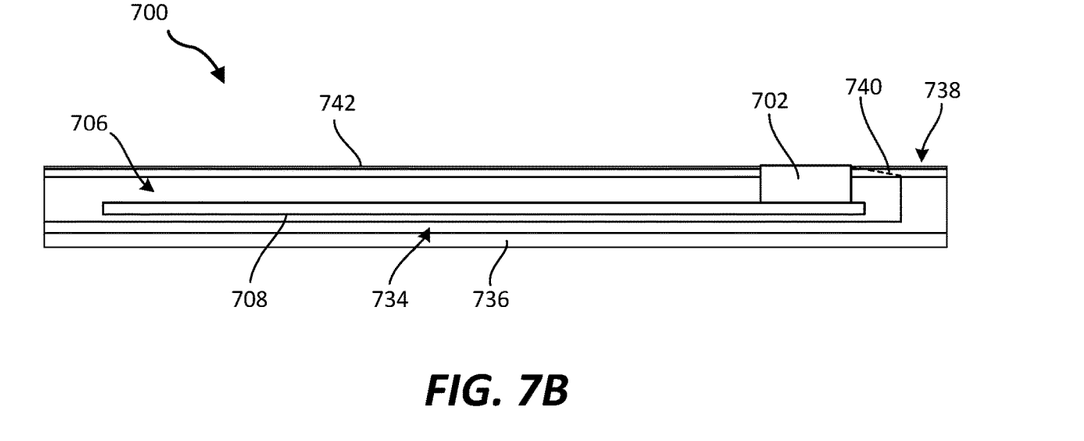
FIG. 7B is a cross-sectional side view of the device of FIG. 7A, taken at line A-A of FIG. 7A.
Figure 8:
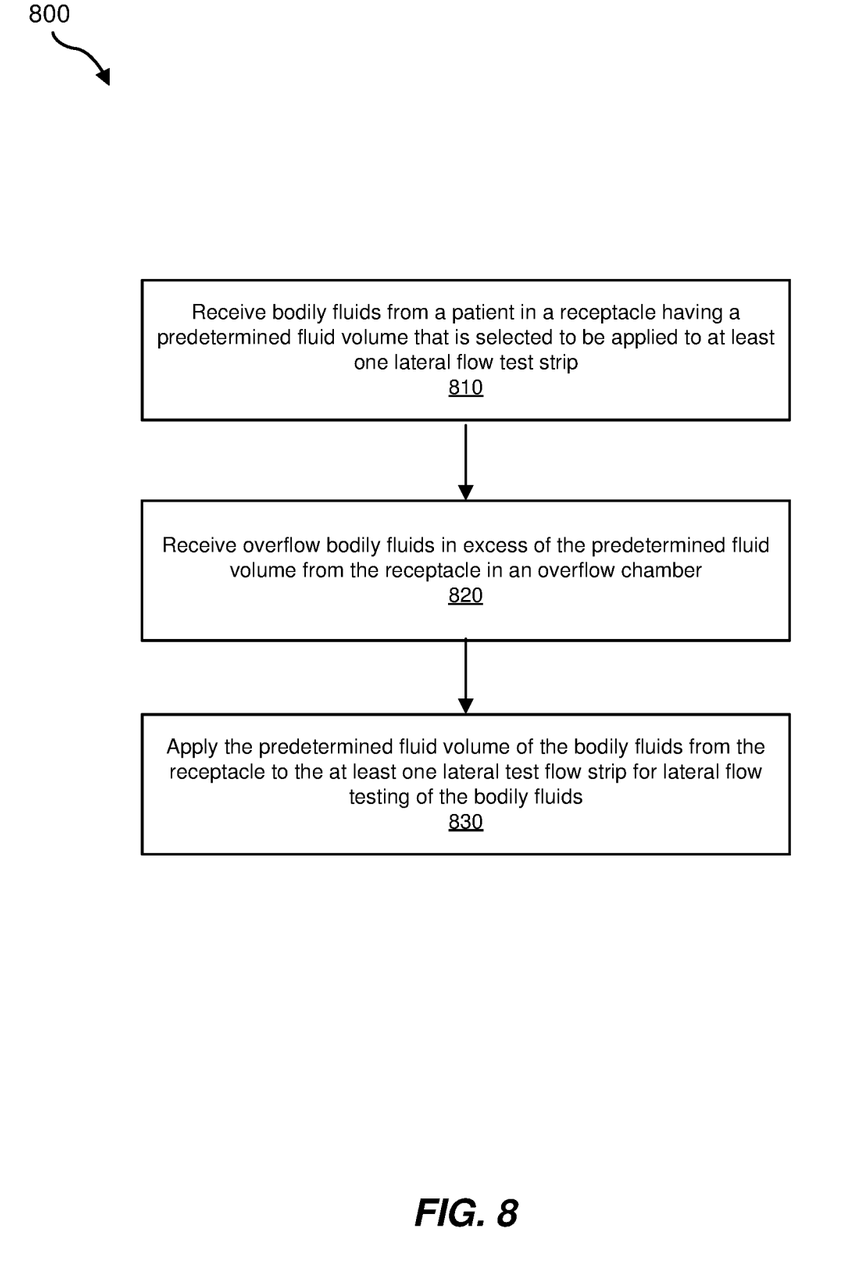
FIG. 8 is a flow chart illustrating a method of lateral flow testing of bodily fluids, according to at least one other embodiment of the present disclosure.

FIG. 7A is a perspective view of a device 700 for lateral flow testing of bodily fluids, according to at least one additional embodiment of the present disclosure. FIG. 7B is a cross-sectional side view of the device 700 of FIG. 7A, taken at line A-A of FIG. 7A.

The device 700 may include one or more receptacles 702 for receiving bodily fluids from a patient. Each of the receptacles 702 may have a predetermined fluid volume that may be selected to be applied to at least one corresponding lateral flow test strip 708 in a test strip holder 706. The device 700 may also include at least one overflow chamber 734 for receiving excess bodily fluids, such as bodily fluids that may overflow from the receptacle 702. For example, as illustrated in FIG. 7B, the overflow chamber 734 may be positioned under the test strip holder 706. An absorbent material 736 (e.g., a sponge, fabric, etc.) may be positioned in the overflow chamber 734 and may be configured to absorb and hold the excess bodily fluid within the overflow chamber 734, such as to reduce or eliminate spilling of the excess bodily fluid out of the overflow chamber 734.

One or more openings 738 in an upper surface 740 of the device 700 may provide fluid access to the overflow chamber 734. In some examples, the opening(s) 738 may be positioned at a lower elevation than an upper edge of the receptacles 702. The upper surface 740 may slope downward from the upper edge of the receptacles 702 to the opening(s) 738, as shown in FIG. 7B. Thus, any excess bodily fluids may flow from the receptacles 702 downward to the opening(s) 738 and ultimately into the overflow chamber 734. In some examples, the upper surface 740 may be coated with a hydrophilic coating, such that the excess bodily fluids do not stick to the upper surface 740 and readily flow toward the overflow chamber 734.

In some embodiments, a transparent covering 742 may be positioned over the test strip holder 706 to inhibit any excess bodily fluids from inadvertently reaching the lateral flow test strips 708, other than through the receptacles 702 as intended. A lip 744 may extend upward from the upper surface 740 along a peripheral edge of the device 700, such as to inhibit spilling any of the excess bodily fluids over the peripheral edge of the device 700.

Although four lateral flow test strips 708 are shown in the device 700 of FIG. 7A, the present disclosure is not so limited. In additional embodiments, the test strip holder 706 may be sized to accommodate one, two, three, or more than four lateral flow test strips 708. The device 700 may include one, two, three, four, or more than four corresponding receptacles 702. In additional embodiments, the device 700 may include a single receptacle 702 for receiving bodily fluids from a patient, and the bodily fluids may be diverted for application to one or more lateral flow test strips 708.

In operation, a user may provide bodily fluids from a patient into the receptacle(s) 702 until the receptacle(s) 702 overflow to ensure that the predetermined fluid volume of the receptacle(s) 702 is full of the bodily fluids. Excess bodily fluids may flow through the opening(s) 738 and into the overflow chamber 734. The bodily fluids from the receptacle(s) 702 may be applied to the lateral flow test strip(s) 708 and tested for the presence and/or quantity of the target substance(s), as described above with reference to FIGS. 1A-1C. After a given time (depending on the lateral flow test strip(s) 708 used), the lateral flow test strip(s) 708 may provide an indication of the presence and/or quantity of the target substance(s) in the bodily fluids. After the results of the test are obtained, the device 700, including any excess bodily fluids that may remain within the overflow chamber 734, may be discarded, such as in an appropriate biohazard waste container.

FIG. 8 is a flow chart illustrating a method 800 of lateral flow testing of bodily fluids, according to at least one other embodiment of the present disclosure. By way of example and not limitation, the method 800 may be performed using any of the devices 100, 700 discussed above with reference to FIGS. 1A-1C, 7A, and 7B.

At operation 810, bodily fluids from a patient may be received in a receptacle. The receptacle may have a predetermined fluid volume that is selected to be applied to at least one lateral flow test strip. Operation 810 may be performed in a variety of ways. For example, bodily fluids including at least one of blood, urine, saliva, and/or effluent from a peritoneal dialysis treatment may be received in the receptacle. The bodily fluids may be introduced into the receptacle by pouring, injection, flowing through a conduit, etc. By way of example, the bodily fluids may be received from the patient in a clinic (e.g., doctor's office, testing facility, etc.), in a care facility, or in the patient's home.

At operation 820, overflow bodily fluids in excess of the predetermined fluid volume from the receptacle may be received in an overflow chamber. Operation 820 may be performed in a variety of ways. For example, a user may stop applying bodily fluids to the receptacle when the user observes the bodily fluids overflowing from the receptacle. Any of the excess bodily fluids may flow into the overflow chamber through one or more openings in an upper surface adjacent to the receptacle. For example, the upper surface may be sloped downward from an upper edge of the receptacle toward the opening(s). In some embodiments, an absorbent material in the overflow chamber may capture and hold the excess bodily fluids.

At operation 830, the predetermined fluid volume of the bodily fluids from the receptacle may be applied to at least one lateral flow test strip for lateral flow testing of the bodily fluids. Operation 830 may be performed in a variety of ways. For example, gravity may cause the bodily fluids within the receptacle to be applied to the lateral flow test strip(s). In the case of multiple lateral flow test strips, the bodily fluids may be directed to the multiple lateral flow test strips by a flow diverter.

Accordingly, the present disclosure includes devices and methods for lateral flow testing of bodily fluids. Devices according to embodiments of the present disclosure may enable users to confidently apply a sufficient amount of bodily fluids to lateral flow test strips for effective testing, without causing problems that may be associated with the application of too much bodily fluids to the lateral flow test strips. Additionally, the devices may be simple to use and relatively inexpensive to manufacture.

The following example embodiments are also included in the present disclosure.

Example 1: A device for lateral flow testing of bodily fluids, which may include: a first receptacle for receiving bodily fluids from a patient, the first receptacle having a first fluid volume; a second receptacle positioned and configured to receive bodily fluids from the first receptacle, the second receptacle having a predetermined second fluid volume selected to be applied to at least one lateral flow test strip; and a test strip holder shaped to receive the at least one lateral flow test strip, wherein the test strip holder is positioned to receive the second fluid volume of bodily fluids from the second receptacle to test the bodily fluids via lateral flow along the at least one lateral flow test strip.

Example 2: The device of Example 1, wherein the test strip holder is sized to receive multiple lateral flow test strips.

Example 3: The device of Example 1 or Example 2, further including a transfer mechanism to move the fluid from the second receptacle to the test strip holder.

Example 4: The device of Example 3, wherein the transfer mechanism includes a rotating piston configured to rotate the second receptacle from a first position to receive the second fluid volume of the bodily fluids from the first receptacle to a second position to pass the second fluid volume of the bodily fluids from the second receptacle to the test strip holder.

Example 5: The device of Example 3 or Example 4, wherein the transfer mechanism includes a syringe configured to draw the second fluid volume of the bodily fluids from the first receptacle into the second receptacle and to pass the second fluid volume of the bodily fluids from the second receptacle to the test strip holder.

Example 6: The device of any of Examples 3 through 5, wherein the transfer mechanism includes: a catalyst chamber in fluid communication with the first receptacle, the catalyst chamber configured to hold a catalyst that expands upon exposure to a sufficient volume of the bodily fluids; a rotating piston including the second receptacle; and a screw thread configured to rotate the rotating piston upon expansion of the catalyst into a position to pass the second fluid volume of the bodily fluids from the second receptacle into the test strip holder.

Example 7: The device of any of Examples 1 through 6, further including a lid for covering the first receptacle.

Example 8: The device of any of Examples 1 through 7, wherein the test strip holder is removable and replaceable relative to the first receptacle and second receptacle.

Example 9: A method of lateral flow testing of bodily fluids, which may include: receiving bodily fluids from a patient in a first receptacle having a first fluid volume; passing a portion of the bodily fluids from the first receptacle to a second receptacle having a predetermined second fluid volume that is selected to be applied to at least one lateral flow test strip; and applying the second fluid volume of the bodily fluids from the second receptacle to the at least one lateral flow test strip for lateral flow testing of the bodily fluids.

Example 10: The method of Example 9, wherein receiving the bodily fluids from the patient includes receiving at least one of the following bodily fluids: blood; urine; saliva; or effluent from a peritoneal dialysis treatment.

Example 11: The method of Example 9 or Example 10, wherein applying the second fluid volume of the bodily fluids from the second receptacle to the at least one lateral flow test strip includes rotating a piston including the second receptacle from a first position to a second position.

Example 12: The method of any of Examples 9 through 11, wherein: passing the portion of the bodily fluids from the first receptacle to the second receptacle includes drawing the portion of the bodily fluids from the first receptacle into the second receptacle with a syringe; and applying the second fluid volume of the bodily fluids from the second receptacle to the at least one lateral flow test strip includes injecting the second fluid volume of the bodily fluids into fluid communication with the at least one lateral flow test strip with the syringe.

Example 13: A device for lateral flow testing of bodily fluids, which may include: a receptacle for receiving bodily fluids from a patient, the receptacle having a predetermined fluid volume selected to be applied to at least one lateral flow test strip; an overflow chamber for receiving the bodily fluids in excess of the predetermined fluid volume; and a test strip holder shaped to receive the at least one lateral flow test strip, wherein the test strip holder is positioned to receive the predetermined fluid volume of bodily fluids from the receptacle to test the bodily fluids via lateral flow along the at least one lateral flow test strip.

Example 14: The device of Example 13, wherein the overflow chamber is positioned under the test strip holder.

Example 15: The device of Examples 13 or Example 14, wherein an upper surface of the device slopes downward from an edge of the receptacle to an opening of the overflow chamber.

Example 16: The device of any of Examples 13 through 15, wherein the overflow chamber includes a plurality of openings to receive the bodily fluids that overflow from the receptacle.

Example 17: The device of Example 16, wherein the plurality of openings are positioned along an end of the device adjacent to the receptacle and along lateral sides of the device.

Example 18: The device of any of Examples 13 through 17, wherein the test strip holder is sized and configured to receive a plurality of lateral flow test strips.

Example 19: The device of Example 18, wherein the receptacle comprises a plurality of receptacles corresponding to the plurality of lateral flow test strips, wherein each receptacle of the plurality of receptacles has a predetermined fluid volume selected to be applied to one corresponding lateral flow test strip of the plurality of lateral flow test strips.

Example 20: The device of any of Examples 13 through 19, further comprising an absorbent material positioned in the overflow chamber and configured to absorb and hold the bodily fluids in excess of the predetermined fluid volume.

Example 21: A method of lateral flow testing of bodily fluids, which may include: receiving bodily fluids from a patient in a receptacle having a predetermined fluid volume that is selected to be applied to at least one lateral flow test strip; receiving overflow bodily fluids in excess of the predetermined fluid volume from the receptacle in an overflow chamber; and applying the predetermined fluid volume of the bodily fluids from the receptacle to the at least one lateral flow test strip for lateral flow testing of the bodily fluids.

Example 22: The method of Example 21, wherein receiving the overflow bodily fluids in excess of the predetermined fluid volume from the receptacle in the overflow chamber includes flowing the overflow bodily fluids downward from an upper edge of the receptacle to at least one opening of the overflow chamber.

Example 23: The method of Example 21 or Example 22, wherein applying the predetermined fluid volume of the bodily fluids from the receptacle to the at least one lateral flow test strip includes flowing the overflow bodily fluids downward from an upper edge of the receptacle to at least one opening of the overflow chamber.

The preceding description has been provided to enable others skilled in the art to best utilize various aspects of the example embodiments disclosed herein. This example description is not intended to be exhaustive or to be limited to any precise form disclosed. Many modifications and variations are possible without departing from the spirit and scope of the present disclosure. The embodiments disclosed herein should be considered in all respects illustrative and not restrictive. Reference should be made to the appended claims and their equivalents in determining the scope of the present disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A device for lateral flow testing of bodily fluids, the device comprising:
   a first receptacle for receiving bodily fluids from a patient, the first receptacle having a first fluid volume;
   a second receptacle positioned and configured to receive bodily fluids from the first receptacle, the second receptacle having a predetermined second fluid volume selected to be applied to at least one lateral flow test strip;
   a test strip holder shaped to receive the at least one lateral flow test strip, wherein the test strip holder is positioned to receive the second fluid volume of the bodily fluids from the second receptacle to test the bodily fluids via lateral flow along the at least one lateral flow test strip; and
   a transfer mechanism to move the bodily fluids from the second receptacle to the test strip holder, wherein the transfer mechanism comprises a rotating piston configured to rotate the second receptacle from a first position to receive the second fluid volume of the bodily fluids from the first receptacle to a second position to pass the second fluid volume of the bodily fluids from the second receptacle to the test strip holder.

2. The device of claim 1, wherein the test strip holder is sized to receive multiple lateral flow test strips.

3. The device of claim 1, further comprising a lid for covering the first receptacle.

4. The device of claim 1, wherein the test strip holder is removable and replaceable relative to the first receptacle and second receptacle.

5. The device of claim 3, wherein the lid is configured to provide a fluid-tight seal over the first receptacle.

6. The device of claim 1, wherein the first fluid volume is larger than the second fluid volume.

* * * * *